United States Patent
Klemm et al.

(10) Patent No.: US 8,466,638 B2
(45) Date of Patent: Jun. 18, 2013

(54) METHOD AND DEVICE FOR ADJUSTING THE FREQUENCY OF A DRIVE CURRENT OF AN ELECTRIC MOTOR

(75) Inventors: Torsten Klemm, Eschborn (DE); Ingo Vetter, Karben (DE); Uwe Jungnickel, Koenigstein (DE)

(73) Assignee: The Procter & Gamble Company, Cincinnati, OH (US)

( * ) Notice: Subject to any disclaimer, the term of this patent is extended or adjusted under 35 U.S.C. 154(b) by 461 days.

(21) Appl. No.: 12/854,956

(22) Filed: Aug. 12, 2010

(65) Prior Publication Data

US 2011/0080122 A1    Apr. 7, 2011

(30) Foreign Application Priority Data

Aug. 12, 2009  (EP) .................................... 09010381

(51) Int. Cl.
    *A61C 17/34*    (2006.01)
(52) U.S. Cl.
    USPC ............ 318/119; 15/22.1; 15/167.1; 318/129
(58) Field of Classification Search
    USPC ................ 318/606, 607, 686, 119, 129, 443, 318/444, 459, 807; 15/21.1, 22.1, 22.2, 167.1
    See application file for complete search history.

(56) References Cited

U.S. PATENT DOCUMENTS

| | | | | |
|---|---|---|---|---|
| 4,275,363 | A | * | 6/1981 | Mishiro et al. ..................... 331/4 |
| 4,320,448 | A | | 3/1982 | Okuda et al. |
| 5,189,751 | A | * | 3/1993 | Giuliani et al. ................. 15/22.1 |
| 5,294,896 | A | * | 3/1994 | Kjellander et al. ............ 331/158 |
| 5,613,259 | A | * | 3/1997 | Craft et al. ...................... 15/22.1 |
| 5,955,799 | A | * | 9/1999 | Amaya et al. .................... 310/36 |
| 6,437,524 | B1 | | 8/2002 | Dimanstein |
| 7,315,098 | B2 | * | 1/2008 | Kunita et al. .................... 310/15 |
| 8,032,965 | B2 | * | 10/2011 | Asada et al. ................... 15/22.1 |
| 8,288,970 | B2 | * | 10/2012 | Miller et al. ................... 318/119 |
| 8,314,586 | B2 | * | 11/2012 | Lumbantobing et al. ..... 318/807 |
| 2003/0006880 | A1 | * | 1/2003 | Zimmer ..................... 340/10.34 |
| 2003/0233877 | A1 | | 12/2003 | Grez et al. |
| 2008/0095641 | A1 | | 4/2008 | Choi et al. |

FOREIGN PATENT DOCUMENTS

| | | |
|---|---|---|
| DE | 102004029684 | 12/2005 |
| EP | 1487091 | 12/2004 |
| WO | WO2008053441 | 5/2008 |

OTHER PUBLICATIONS

International Search Report, mail date Sep. 14, 2010, 4 pages.
Written Opinion of the International Search Report; 7 pages.

* cited by examiner

*Primary Examiner* — Bentsu Ro
(74) *Attorney, Agent, or Firm* — Kim William Zerby; Brent Matthew Peebles

(57) ABSTRACT

A small electric appliance is described which comprises an oscillation-capable mechanism (4), an electric motor (1) to drive the oscillation-capable mechanism (4), wherein the electric motor (1) can be operated with a drive current (10) at a predetermined frequency (f), and a device (3) for adjusting the frequency (f) of the drive current of the electric motor (1). Furthermore, a method for adjusting the frequency (f) of a drive current (10) of an electric motor is described comprising the following steps of detecting, at a specified time ($t_{meas}$), in relation to the period of the drive current, an electric variable (20) generated by the electric motor (1)

determining, at the specified measuring time ($t_{meas}$), whether the detected electric variable (20) essentially has a zero-crossing and changing the frequency (f) of the drive current until the detected electric variable (20) essentially has a zero-crossing at the measuring time ($t_{meas}$).

13 Claims, 3 Drawing Sheets

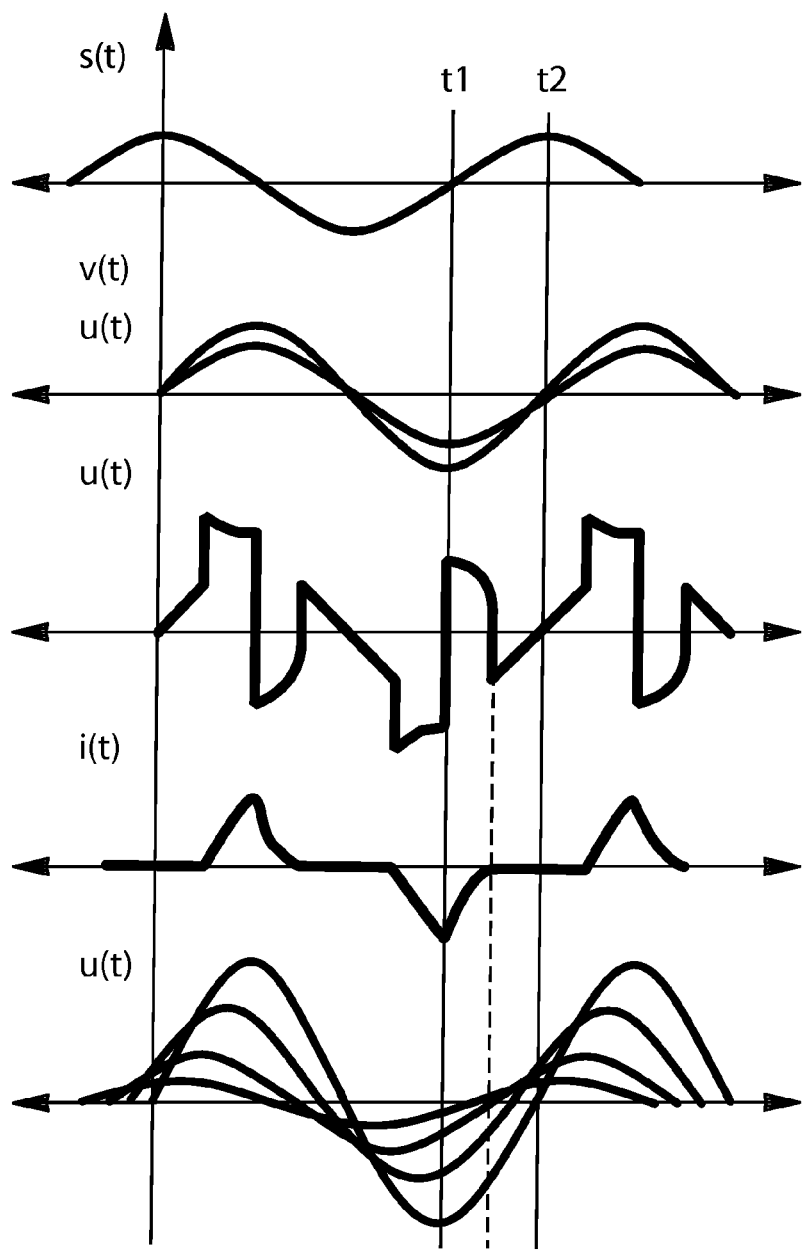

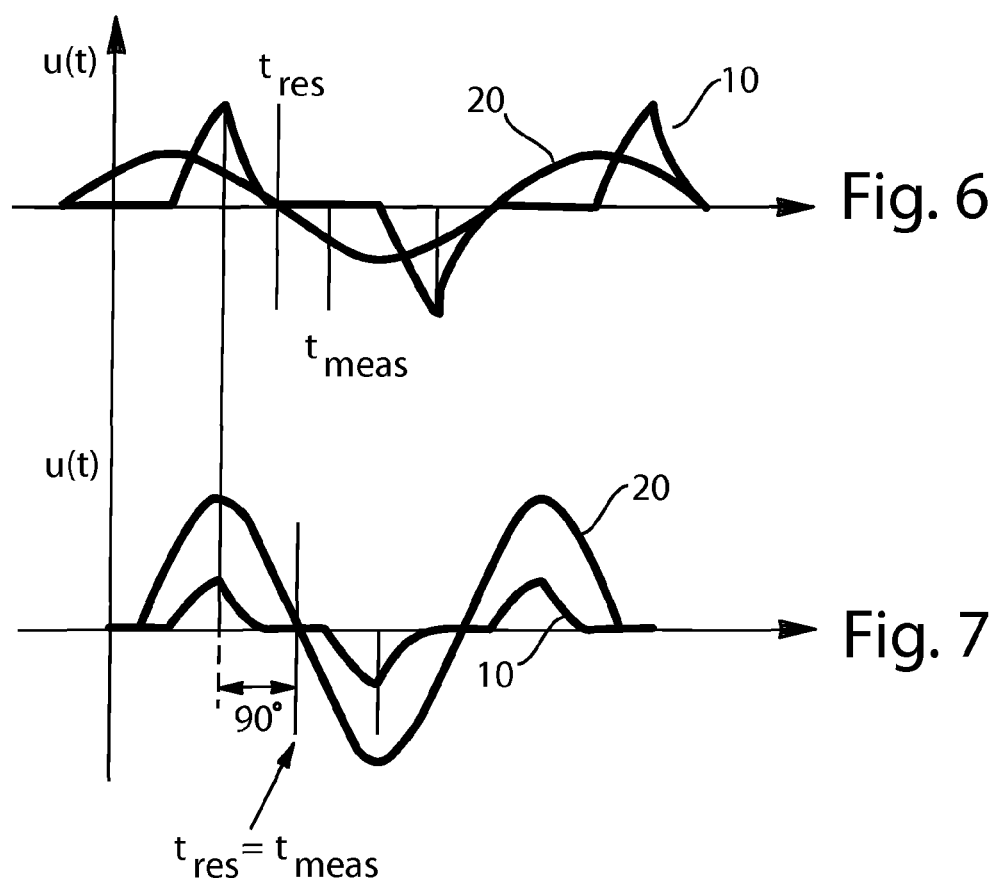

METHOD AND DEVICE FOR ADJUSTING THE FREQUENCY OF A DRIVE CURRENT OF AN ELECTRIC MOTOR

FIELD OF THE INVENTION

The invention relates to a method and device for adjusting the frequency of a drive current of an oscillating electric motor that is preferably provided for a small electric appliance, for example an electric toothbrush or an electric shaving apparatus with a mechanism capable of oscillating, which may be driven by the oscillating electric motor.

BACKGROUND OF THE INVENTION

In small electric appliances, an oscillating direct drive, such as an oscillating electric motor, can be provided to drive mechanical parts capable of oscillation. Such types of drives are used, for example, in electric razors or electric toothbrushes whose working amplitude is generated without gearing. The mechanical parts capable of oscillation are primarily the rotors of the oscillating electric motor, the drive shaft, and optionally a component coupled to the drive shaft, for example a replaceable brush. In order to achieve a high level of efficiency, it is desirable for the oscillating electric motor to be operated with alternating current whose frequency takes into consideration the resonance frequency of the oscillating mechanical parts of the small appliance.

Determination of the resonance condition to drive oscillation-capable mechanical parts via the power consumption of the electric motor or the working amplitude of the oscillating parts is known. The disadvantage of this is that quantitative measuring processes must be carried out, for example, to determine the minimum of the current or the maximum of the working amplitude. To that end, measuring equipment must be provided for carrying out the measuring processes.

From German published patent application DE 10 2004 029 684 A1 is known the determination of the resonance condition to drive oscillation-capable mechanical parts via an analysis of a die-out oscillation process of the mechanical parts over time. To do this, the electric motor is switched on for a short period of time so that it can execute a few oscillation movements and the oscillation-capable parts can achieve a state of resonance. The electric motor is then switched off so that the oscillation movements of the electric motor die out. During this process, the electric motor generates induced voltage corresponding to the oscillation movements for a brief period. The frequency of the induced voltage is measured and then considered in the repeated electric actuation of the electric motor. Quantitative measuring processes are also used here, which have the previously mentioned disadvantages. A further disadvantage exists in that the results of the analysis of the die-out oscillation process depend on the damping properties of the oscillation-capable mechanical components.

If the damping properties are not known or if the damping properties change over time, this can negatively affect the efficiency of the system.

OBJECT OF THE INVENTION

The object of the invention is to provide a method and a device which enable simple but also sufficiently precise adjustment of the frequency of a drive current of an electric motor.

Achievement of the object according to the invention

This object is achieved through a method and a device according to the claims.

Accordingly, a method is provided for adjusting the frequency of a drive current of an electric motor in a small electric appliance with an oscillation-capable mechanism, which is driven by the electric motor, wherein an electric variable generated by the electric motor is detected at a specified measuring time, in relation to the period of the drive current, wherein, at the specified measuring time, it is determined whether the detected electric variable essentially has a zero-crossing, and wherein the frequency of the drive current is changed until the detected electric variable essentially has a zero-crossing at the measuring time.

By simply determining a zero-crossing of an electric variable at the measuring time, the use of quantitative measuring processes, for example to determine the amount of a current, can be omitted. Since the approximation of the frequency of the drive current to the resonance frequency can occur in any desired small increments, a sufficiently high level of accuracy of the adjustment to the resonance frequency is possible. In this way it is always possible to operate the oscillating system in resonance also in case of fluctuations of the resonance frequency of the mechanical system that may, for instance, be due to load variations.

Advantageously, the measuring time is in the center of half a period of the drive current of the electric motor, because the zero-crossing of the detected electrical variable corresponds to a phase shift of 90° between the detected electric variable and the amplitude maximum (velocity minimum) at this time. It is particularly advantageous when the measuring time is phase-shifted 90° with respect to the maximum of the drive current of the electric motor. The measuring time can also be phase-shifted 90° with respect to the minimum of the drive current of the electric motor.

The electric variable can be the voltage, which is induced by the moving motor in its coil, i.e. the back electromotive force (back EMF), which is also called generator voltage.

After each change in frequency of the drive current, the measuring point in time, in relation to the changed period of the drive current, can be determined. The frequency of the drive current can be changed incrementally in this process.

It is advantageous if the frequency of the drive current, which comes up essentially with a zero-crossing in the counter-induction voltage at the measuring time, is stored and provided to the control electronics of the small electric appliance. The stored frequency can then be used for later adjustment of the frequency of the drive current to the resonance frequency, as a starting frequency of the drive current.

Also described is a small electric appliance with an oscillation-capable mechanism, an electric motor to drive the oscillation-capable mechanism, wherein the electric motor can be operated with a drive current of a predetermined frequency, and a device to adjust the frequency of the drive current of the electric motor, wherein the device is designed
  in order to detect an electric variable generated by the electric motor at a specified measuring time, in relation to the period of the drive current
  in order to determine, at the specified measuring time, whether the detected electric variable essentially has a zero-crossing and
  to change the frequency of the drive current until the detected electric variable essentially has a zero-crossing at the measuring time.

SHORT DESCRIPTION OF THE FIGURES

The invention is explained in more detail using an exemplary embodiment, which is shown in the drawings.

FIGS. 1-4 show the relationships between the movement of an oscillating system of a small electric appliance and the electric variables of control electronics;

FIG. 5 shows a continuously adapted back EMF as the frequency of the drive current changes;

FIG. 6 shows the electric values of a system in which the resonance conditions are not fulfilled;

FIG. 7 shows the electric values of a system in which the resonance conditions are fulfilled.

EXEMPLARY EMBODIMENT

Figure 8:
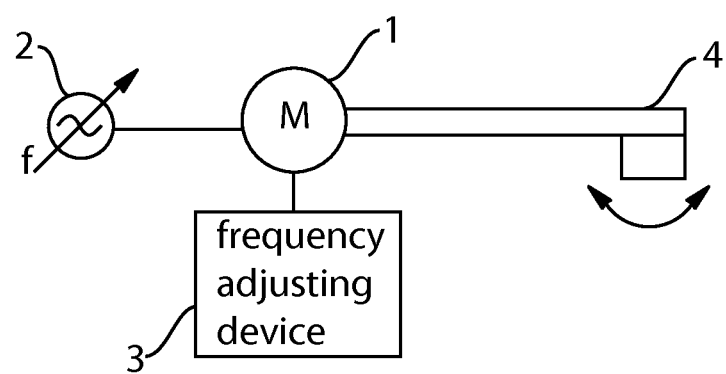
FIG. 8 shows a concept circuit diagram of a small electric appliance.

The method according to the invention is described in more detail using an electric toothbrush that has a commonly known handheld part with an electric motor which, for instance, provides a drive shaft on which a replacement brush is placed. The electric motor can cause the replacement brush to make an oscillation movement. The replacement brush placed at the drive shaft results in a certain mass and, during operation, a certain moment of inertia for the oscillation-capable mechanism, which essentially comprises the rotor of the electric motor, the drive shaft, and the replacement brush, and thus a certain resonance frequency.

Furthermore, the electric toothbrush has a device for adjusting the frequency of the drive current of the electric motor in order to change the frequency of the drive current such that it is in the proximity of the resonance frequency. This results in a high level of efficiency for the electric toothbrush.

The procedure according to which the frequency of the drive current is changed and which is executed by the adjusting device is explained below. To that end and with reference to FIGS. 1 through 4, the relationships between the movement of an oscillating system and the electric variables of control electronics and/or an electric motor of a small electric appliance are explained.

FIG. 1 shows the oscillating movement s(t) of an oscillating system, for example of the rotor of the electric motor, the drive shaft, and the replacement brush of an electric toothbrush, over time.

FIG. 2 shows the speed v(t) of the electric motor and the back EMF u(t) at one coil of the electric motor over time. The back EMF u(t) is, together with the motor constant of the electric motor, proportional to the speed v(t) of the electric motor.

FIGS. 3 and 4 show the drive voltage u(t) and the drive current i(t) of control electronics to drive the electric motor at one coil. In the phases without drive current, i.e. when i(t)=0, it is possible to directly measure at this coil the back EMF of the electric motor shown in FIG. 2. However, a quantitative statement about the amplitude of the back EMF shown in FIG. 2 is only possible if the measurement and/or the evaluation always takes place at a specific time in relation to t2.

With the method described, it is possible to adjust the drive current to the resonance frequency of an oscillating system without a quantitative measuring process. To that end, the frequency f of the drive current is changed until the drive current is in a state of resonance with the oscillating system. The resonance condition in this process is recognized by the phase shift between the drive current and the oscillating system becoming 90°. The level of efficiency in this case is the maximum.

The resonance condition is specified by determining whether the back EMF essentially has a zero-crossing at a predetermined measuring time $t_{meas}$, in relation to the period of the drive current. Preferably, the measuring time $t_{meas}$ is the center of half a period of the drive current, i.e. measured starting from the maximum of the drive current, at a phase shift of ±90° of the drive current.

If the back EMF does not have a zero-crossing at the measuring time $t_{meas}$, the frequency f of the drive current is changed, preferably by a predetermined value. After a change in the frequency f of the drive current, the measuring time $t_{meas}$ is determined again in relation to the new period of the drive current, and a check is carried out to determine whether the back EMF then has a zero-crossing.

This process is repeated until the back EMF has a zero-crossing at the measuring time $t_{meas}$. When the back EMF has a zero-crossing with a phase shift of ±90° with respect to the maximum of the drive current, the drive current is in a state of resonance with the oscillating system. The phase shift between the drive current and the oscillating system is then also 90°. FIG. 5 shows continuous adaptation of the frequency of the back EMF, which results from the adaptation of the frequency of the drive current.

Particularly advantageous in the method described is that the zero-crossing of the back EMF can be detected very easily electrically.

FIG. 6 shows an example of a system in which the phase relationship between the drive current and the oscillating system is not fulfilled, which means that the drive current is not in a state of resonance with the oscillating system. FIG. 6 shows that the zero-crossing of the back EMF 20 is not at the measuring time $t_{meas}$ of the drive current 10. In this case, the measuring point in time $t_{meas}$ is phase-shifted 90° with respect to the maximum of the drive current.

FIG. 7 shows an example in which the phase relationship between the drive current 10 and the oscillating system is fulfilled. The drive current in this case is in a state of resonance with the oscillating system. The zero-crossing of the back EMF 20 is located at the measuring time $t_{meas}$ of the drive current 10. The back EMF 20 and the drive current 10 are phase-shifted 90° with respect to the oscillating system and are in a state of resonance with said system.

The actual measuring point in time in this case represents a measuring angle, which is a percentage of the period duration of the frequency of the drive current. The method described also functions when the phase shift, i.e. the measuring angle, is not exactly 90°; however, the deviation from the measuring angle of 90° is considered in the actuation of the electric motor.

An advantage of the described method exists in that a very high level of accuracy in the resonance frequency of the oscillating system can be achieved with minimal technical effort on the part of the actuation equipment, because the actuation equipment only has to provide uncontrolled frequencies and, in order to evaluate the phase relationship, only the determination of whether there is a zero-crossing of the back EMF at the measuring time is required.

The frequency f of the drive current can be increased or decreased incrementally until there is a phase shift of 90° between the drive current and the oscillating system, in relation to the maximum or minimum of the drive current. In one embodiment of the invention, the increments can be large at the beginning and decreased as time goes on. This enables the frequency f of the drive current to very quickly approximate the resonance frequency of the oscillating system. The frequency of the drive current determined according to the method described can be stored, for example, in the actuation equipment and used as the starting frequency for the next adjustment process.

It is advantageous in that complex equipment for quantitative measuring processes, for example to determine the current minimum, is no longer required. A further advantage exists in that initial oscillator tolerances of the actuation equipment can be eliminated almost completely, because the last stored frequency was stored on the basis of this tolerance.

The costs for the entire system are kept low, because components such as comparators or voltages references are not needed. Electronic PC boards can be produced more compactly.

FIG. 8 shows a concept circuit diagram of an electric toothbrush. The electric toothbrush essentially comprises an electric motor 1, a power source 2, a device 3 for adjusting the frequency of the drive current for the electric motor 1, and a toothbrush 4 that can be driven by the electric motor.

The toothbrush 4 is a component of the oscillation-capable mechanism of the electric toothbrush. The electric motor 1 is supplied from the power source 2, wherein the frequency f of the current of the power source is adjustable and/or controllable.

The device 3 is designed such that it can specify a measuring point in time, in relation to the period of the drive current, for detecting a back EMF generated by the electric motor 1, that it can determine, at a specified measuring time $t_{meas}$, whether the back EMF essentially has a zero-crossing, and that it can change the frequency f of the drive current until a zero-crossing of the back EMF is essentially present at the measuring time. The device 3 thus determines, at a predetermined time, whether a zero-crossing of the back EMF of the electric motor 1 is present and changes, dependent thereupon, the frequency f of the current of the power source 2.

If the pressure with which the toothbrush is pressed against the teeth changes in teeth cleaning, also the mechanical resonance frequency of the oscillation-capable system will change since the moment of inertia of a toothbrush that is more pressed together differs from that of a toothbrush that is less pressed together. With the method described the toothbrush may also under such circumstances be always operated in resonance by correspondingly readjusting the frequency of the drive current.

The method described is not limited to usage in electric toothbrushes. Rather, it can also be used in other electric appliances with oscillating direct drives, such as, for example, electric shaving apparatuses or household appliances. In like manner, the small electric appliance described can be not just an electric toothbrush but also an electric shaving apparatus or household appliances.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for adjusting the frequency (f) of a drive current of an electric motor in a small electric appliance with an oscillation-capable mechanism, which is driven by the electric motor, wherein an electric variable generated by the electric motor is detected at a specified measuring time ($t_{meas}$), in relation to the period of the drive current, wherein, at the specified measuring time ($t_{meas}$), it is determined whether the detected electric variable essentially has a zero-crossing, and wherein the frequency (f) of the drive current is changed until the detected electric variable essentially has a zero-crossing at the measuring time ($t_{meas}$).

2. The method according to claim 1, wherein, in relation to the maximum or minimum of the drive current, the measuring time ($t_{meas}$) is in the center of half a period of the drive current of the electric motor.

3. The method according to claim 1, wherein the electric variable is the back electromotive force at one coil of the electric motor.

4. The method according to claim 3, wherein, after each change in the frequency (f) of the drive current, the measuring time ($t_{meas}$) is determined, in relation to the changed period of the drive current.

5. The method according to claim 4, wherein the frequency of the drive current is changed incrementally.

6. The method according to claim 4, wherein the frequency of the drive current, which essentially has a zero-crossing in the back electromotive force at the measuring time ($t_{meas}$), is stored and provided to a control electronics of the small electric appliance.

7. The method according to claim 1, wherein the small electric appliance is an electric shaving apparatus or an electric toothbrush.

8. A small electric appliance with an oscillation-capable mechanism, an electric motor to drive the oscillation-capable mechanism, wherein the electric motor can be operated with a drive current at a predetermined frequency (f), and a device for adjusting the frequency (f) of the drive current of the electric, motor, wherein the device is designed
in order to detect, at a specified time ($t_{meas}$), in relation to the period of the drive current, an electric variable generated by the electric motor
in order to determine, at the specified measuring time ($t_{meas}$), whether the detected electric variable essentially has a zero-crossing and
to change the frequency (t) of the drive current until the detected electric variable essentially has a zero-crossing at the measuring time ($t_{meas}$).

9. The small electric appliance according to claim 8, wherein the measuring time ($t_{meas}$) is in the center of half a period of the drive current.

10. The small electric appliance according to claim 8, wherein the electric variable is the back electromotive force at one coil of the electric motor.

11. The small electric appliance according to claim 10, wherein the frequency of the drive current of the electric motor is continuously modified until essentially a zero-crossing of the back electromotive force is present at the measuring time ($t_{meas}$), wherein, after each change in frequency (f) of the drive current, the measuring time ($t_{meas}$) is determined in relation to the changed period of the drive current.

12. The small electric appliance according claim 8, which is designed as an appliance for personal use.

13. The small electric appliance according to claim 12 wherein the small electric appliance is designed for use as an electric toothbrush or an electric shaving apparatus.

* * * * *